United States Patent [19]

Edgar et al.

[11] Patent Number: 4,997,946

[45] Date of Patent: Mar. 5, 1991

[54] PROCESS FOR THE IODINATION OF HYDROXYAROMATIC AND AMINOAROMATIC COMPOUNDS

[75] Inventors: Kevin J. Edgar; Guy R. Steinmetz, both of Kingsport, Tenn.

[73] Assignee: Eastman Kodak Company, Rochester, N.Y.

[21] Appl. No.: 86,478

[22] Filed: Aug. 18, 1987

[51] Int. Cl.$^5$ ................ C07D 215/18; C07D 213/61; C07C 39/26

[52] U.S. Cl. .................................. 546/179; 546/303; 568/779

[58] Field of Search ................ 546/303, 179; 560/779

[56] References Cited

U.S. PATENT DOCUMENTS

| | | | |
|---|---|---|---|
| 2,835,700 | 5/1958 | Boyle | 546/179 |
| 3,363,010 | 1/1968 | Schwarzenbek | 568/779 |
| 3,549,593 | 12/1970 | Takekoshi | 260/584 |
| 4,026,946 | 5/1977 | Quinlan | |

FOREIGN PATENT DOCUMENTS

| | | | |
|---|---|---|---|
| 3142654 | 5/1983 | Fed. Rep. of Germany | |
| 5079 | 2/1890 | United Kingdom | 568/779 |

OTHER PUBLICATIONS

S. A. Glover et al.; "Role of Tert-Butyl Hypoiodite in Aromatic Iodination Reactions with Tert-Butyl Hypochlorite-iodine Reagent", Chemical Abstracts, vol. 80, No. 3, Jan. 21, 1974, (Columbus, Ohio, U.S.), p. 368, Abstract 14224Q & J. S. Afr. Chem. Inst. 1973, 26(3), 77-81 (Eng).

*Tetrahedron Letters*, (1986), vol. 27, No. 49, pp. 5963-5966, "On the Product Distribution in the Iodination of Phenol"; R. De Rossi, et al.

*J. Org. Chem.* (1987), vol. 52, pp. 664-667, "Use of Aryltrimethylgermanium Substrates for Facile Aromatic Chlorination, Bromination and Iodination"; S. M. Moerlein.

*Chemistry Letters* (1987), pp. 2109-2112, "Iodination of Phenols by Use of Benzyltrimethylammonium Dichloroiodate (1-)$^{1)}$"; Shoji Kajigaeshi et al.

*The Chemical Society of Japan*, (1988), vol. 61, No. 2, pp. 600-602, "Halogenation Using Quaternary Ammonium Polyhalides. VII(1) Iodination of Aromatic Amines by Use of Benzyltrimethylammonium Dichloroiodate(1-)"; Shoji Kajigaeshi, et al.

*Tetrahedron Letters* (1986), pp. 2207-2210, "The Iodination of Aromatic Substrates on Alumina", vol. 27, No. 20, Richard Boothe, et al.

*Indian Journal of Chemistry*, (1987), vol. 26A, pp. 333-335, "Electrophilic Aromatic Substitution Reactions: Part III—Iodination of Anilines with Iodine Monochloride in Presence & Absence of a Surfactant"; G. V. S. Shashidhar et al.

*Tetrahedron Letters*, (1985), vol. 26, No. 17, pp. 2043-2046, "Iodination of Phenols Using Chloramine T and Sodium Iodide"; T. Kometani, et al.

*J. Org. Chem.* (1985), vol. 50, pp. 5384-5387, "An Improved Procedure for the Iodination of Phenols Using Sodium Iodide and Tert-Butyl Hypochlorite"; Tadashi Kometani, et al.

A. L. Palomo-Coll and G. Palomo-Coll, Afinidad, 28, 101 (1951).

R. Sen-Gupta, J. Indian Chem. Soc., 22, 171 (1945).

A. L. Palomo-Coll and G. Palomo-Coll, Affinidad, 28, 163 (1951).

Ger. Pat. 117, 767; Chem Zentralbl., 72, (I), 429 (1901).

A. Claus, Arch. Phar., 231,704 (1893).

L. P. Botton, An. Fac. Farm. Bioquim, Univ. Nac. Mayor San Marcos, Lima, 6, 602, (1955); Chem. Abstr., 52, 18407 (1958).

Ger. Pat. 78,880; Beilstein, Handbuch der Organischen Chemie, 21, 90 (1935).

J. Org. Chem., 1985, 50, pp. 5384-5387, Kometani et al, An Improved Procedure for the Iodination of Phenols Using Sodium Iodide and Tert-Butyl Hypochlorite.

*Primary Examiner*—David B. Springer

*Attorney, Agent, or Firm*—Oblon, Spivak, McClelland, Maier & Neustadt

[57] ABSTRACT

A method of iodinating hydroxyaromatic and aminoaromatic compounds is disclosed, comprising reacting the hydroxyaromatic or aminoaromatic compound with an aqueous solution of a metal iodide and a metal hypochlorite at a temperature about −100° to 100° C. in the presence of an alcohol having 1–10 carbon atoms.

11 Claims, No Drawings

PROCESS FOR THE IODINATION OF HYDROXYAROMATIC AND AMINOAROMATIC COMPOUNDS

BACKGROUND OF THE INVENTION

1. Field of the Invention

The invention relates to a process for iodinating hydroxyaromatic and aminoaromatic compounds economically and under mild conditions using a metal iodide and a metal hypochlorite.

2. Discussion of Background

Iodinated hydroxyaromatic compounds are useful intermediates in the production of hydroxybenzoic acids, which have commercial utility as monomers in the production of liquid crystal polyesters. See for example, U.S. Pat. No. 3,549,593.

Hydroxybenzoic acids may be produced by iodinating a phenolic compound and subsequently carbonylating the iodophenol to produce a hydroxybenzoic acid.

One method of iodinating hydroxyaromatic compounds utilizes an oxyiodination reaction in the presence of zeolite catalysts. See U.S. application Ser. No. 029,897 filed Mar. 25, 1987. The aromatic starting material is passed over the catalyst at relatively high temperatures of between about 100°–500° C. Additionally, starting materials containing alkyl groups cannot be used in the process since the alkyl groups are usually oxidized during the process.

Iodination of hydroxyaromatic compounds using sodium iodide and tertiary-butyl hypochlorite is known. See *J. Org. Chem.*, 50 5384–5387 (1985). This method is undersirable, however, since t-butyl hypochlorite is expensive and unstable and therefore inconvenient to use. Additionally, the method utilizes expensive and toxic solvents such as acetonitrile, and the reaction mixture must be buffered which significantly increases the cost when using the method in an industrial process. Additionally, this method is somewhat non-selective since frequently both mono- and di-substituted products are produced.

Finally, the use of tertiary-butyl hypochlorite appears to be limited to iodinations of phenolic compounds and has not been generalized to other activated aromatic compounds such as aromatic amines, i.e. anilines, hydroxypyridines, or hydroxyquinolines.

Selectivity is important in the iodination of hydroxy and aminoaromatic compounds since this process may be utilized to introduce a radioactive iodine such as for example $131_I$ or $125_I$ into a compound as a radiolabel. Since these iodine isotopes hava a relatively short half life (8 days for $131_I$ and 60 days for $125_I$) and are expensive, a method of introducing the radiolabel must be both efficient and economical. That is, the reaction must be fast and be very selective.

High selectivity is also important since iodinated aromatics are useful intermediates that can be carbonylated or coupled to various polymer intermediates. The carbonylation of p-iodophenol to p-hydroxybenzoic acid is one example where high selectivity to the para isomen is desired.

Known methods of iodinating hydroxyaromatic compounds are relatively non-selective and are therefore inappropriate for such applications.

Accordingly, there exists a need for a selective method of iodination hydroxyaromatic and aminoaromatic compounds.

A further need exists for an iodination method which utilizes inexpensive and nontoxic reagents.

A further need exists for an iodination method which has a short reaction time and which is very selective and therefore is useful in radiolabelling applications.

SUMMARY OF THE INVENTION

Accordingly, one object of the present invention is to provide and iodination method which utilizes inexpensive and non-toxic reagents and which has a short reaction time.

Another object of the invention is to provide a method which is selective and suitable for use in radiolabelling applications.

A further object of the invention is to provide a method which utilizes low temperatures and is highly selective.

These and other objects of the present invention which will become apparent in the following specification have been achieved by the present method comprising the step of:

reacting the hydroxyaromatic or aminoaromatic compound with an aqueous solution of a metal iodide and a metal hypochlorite at a temperature between about −100° to 100° C.

DETAILED DESCRIPTION OF THE PREFERRED EMBODIMENTS

The aromatic compounds which can be utilized in the practice of the present invention are essentially any unsubstituted and substituted hydroxyaromatic and aminoaromatic compounds. Suitable aromatic compounds include hydrocarbon aromatics, nitrogen-containing aromatics, oxygen-containing aromatics and sulfur containing aromatics. Typical hydrocarbon aromatics include benzene and condensed ring aromatics such as naphthalene and anthracene. Typical sulfur containing aromatics are, for example, thiophene and benzothiophene. Typical nitrogen containing aromatics include aniline, pyridine and quinoline. Suitable oxygen-containing aromatics are, for example, furan and benzofuran. Substituted aromatics suitable for use with the present invention include aromatic sulfones, diaryl ethers, diaryl carbonyls, diaryl sulfides and the like.

The aromatic starting materials may be substituted by one or more alkyl groups, preferably alkyl groups having from 1-6 carbon atoms. Especially preferred alkyl groups are methyl, ethyl, propyl, and butyl groups.

Additional substituents on the aromatic compounds may include phenyl, halogen, such as fluoro, iodo, chloro, and bromo, as well as hydroxy, nitro, amino, alkoxy, carboxylate and carboxylic acid substituents, and aryl sulfones and aryl ketones. Preferred starting materials are phenolic compounds, i.e., hydroxybenzenes. Examples of particularly preferred phenolic compounds include phenol, 2-methylphenol, 4-methylphenol, 2, 6-dimethylphenol, 4-nitrophenol, 2-iodophenol, 4-chlorophenol, 2-chlorophenol, 3-ethylphenol, 2-phenylphenol and 2-methoxyphenol. Also particularly preferred are 1-naphthol, 2-naphthol, 2-hydroxypyridine, 3-hydroxypyridine, 8-hydroxyquinoline, and aniline.

The hydroxyaromatic or aminoaromatic starting material is reacted with an aqueous solution of a metal iodine and a metal hypochlorite, optionally in the presence of an alcohol, to produce the iodinated aromatic compound. Metal iodines suitable for use in the present reaction include iodides in which the metal cation is an alkali or alkali earth cation. Although both alkali and alkali earth metal iodides are effective in the present reaction, the alkali metal iodides are preferred since they are generally more soluble under the reaction conditions than the alkaline-earth iodides. Particularly preferred metal iodides are lithium iodide, sodium iodide and potassium iodide, with potassium iodide and sodium iodide being especially preferred.

Metal hypochlorites suitable for use in the present reaction are hypochlorites having an alkali or alkaline-earth cation similar to the metal iodides noted above. Preferred metal hypocholorites are the alkali metal hypochlorites with potasium hypochlorite and sodium hypochlorite being particularly preferred. An especially preferred metal hypochlorite is sodium hypochlorite.

The reaction is performed using an aqueous solution of metal iodide and metal hypochlorite and optionally a polar organic solvent. Suitable polar organic solvents include alcohols having from 1-10 carbon atoms, such as methanol, ethanol, propanol, and tertiary and n-butanol, and also polar aprotic organic solvents including tetrahydrofuran, acetonitrile and dimethylformamide (DMF).

In addition to polar solvents, it is possible to use nonpolar aromatic solvents in the presence of phase transfer agents. Suitable aromatic solvents include benzene, toluene, xylene, etc. A preferred solvent is toluene. Suitable phase transfer catalysts include crown ethers, quaternary ammonium salts, quaternary ammonium or phosphonium salts and cryptates. Preferred phase transfer agents are the quaternary ammonium. salts, with benzyltriethylammonium chloride being especially preferred.

The reaction may be run in aqueous solution alone or, preferably, run in the presence of alcohols having from 1-10 carbon atoms. The presence of alcohols in the reaction medium increases the selectivity and yield of the iodinated aromatic product.

In a preferred embodiment of the present method, a base is added to the reaction medium. The base is thought to act by way of a general base catalysts and the presence of base increases the selectivity and yield of the reaction, favoring monoiodination para to the hydroxyl group, and inhibits the production of chlorine containing products. While any type of base may be added, the base should have a basic equilibrium constant at least equal to that of sodium carbonate. Amines, hydroxides, carbonates, etc. are all suitable as basic catalyst for the process. Preferred bases are sodium carbonates, and sodium hydroxide. The reagents described above are inexpensive, easily available, stable and are non-toxic. Additionally, the reaction solution does not require buffering which further reduces the cost of the process.

The process of the present invention is very selective, producing primarily the monoiodinated product in yields of generally 70-100%.

The reaction is generally carried out at temperatures between about $-100°$ and $100°$ C., although lower temperatures are preferred since they generally give higher selectivities than reactions performed at higher temperatures. A preferred temperature range is $-78°$ to $45°$ C. with $-20°$ to $20°$ C. being particularly preferred.

The rate of the reaction is very fast even at low temperatures. The reaction time is generally equal to the amount of time necessary to add the reagents and remove heat from the reaction mixture. In the presence of general base catalysis, the present reactions are virtually instantaneous. Although the reactions are probably complete within a few minutes, the reaction mixtures are generally stirred for a period of time varying from a few minutes to a few hours to ensure completion of the reaction.

The iodination reaction of the present invention may be performed in a batchwise fashion or may be performed in a semi-batch or continuous process. The choice of operating procedure will depend on the specific reactants and products, as well as engineering considerations, and can be readily determined by one skilled in the art.

The rapid nature of the reaction, the selectivity and the economical nature of the reagents is particularly useful when using the present reaction to introduce radioactive iodine into aromatic compounds. The uses of radioactive iodine for radiolabelling, medical diagnosis and medical treatment are well known to those skilled in the art. See *The Merck Index*, pp. MISC 16-17, 9th Ed.

Other features of the invention will become apparent in the course of the following descriptions of exemplary embodiments which are given for illustration of the invention and are not intended to be limiting thereof.

EXAMPLES

In the procedures utilized in Examples 1-13, 2.00 grams of the hydroxyaromatic compound is loaded into a 100 mL glass flask, equipped with nitrogen inlet, magnetic stir bar, thermometer and addition funnel. One equivalent of sodium iodide is added, and in some cases an equivalent of sodium hydroxide is also added (see specific examples). The solvent (50 mL) is added and the resulting solution is adjusted to reaction temperature. A solution of sodium hypochlorite, containing one equivalent of NaOCl in 1-10% aqueous solution, is added to the addition funnel. The NaOCl solution is added to the reaction mixture dropwise, over the specified period and at the specified temperature. The mixture is held at the specified temperature for a short time period after completion of the NaOCl addition, then the product is isolated by adjustment of the pH of the reaction mixture, followed in most cases by solvent extraction. The yields reported are either of isolated, pure compounds, or are calculated by gas chromatographic analysis of the crude product using internal standard weight percent techniques.

The procedure for Example 14 was similar, except that it employed 100 grams of hydroxyaromatic compound (2-phenylphenol), 500 mL solvent, and the yield is calculated by GC area percent assay of the crude product.

Example 15 demonstrates that the present method works when an aminoaromatic is substituted for the hydroxyaromatic compound.

| | Example No. 1 | Example No. 2 | Example No. 3 | Example No. 4 | Example No. 5 | Example No. 6 | Example No. 7 |
|---|---|---|---|---|---|---|---|
| Hydroxy-aromatic | Phenol | Phenol | Phenol | Phenol | 2-Naphthol | 2-Cresol | 2-Iodo-phenol |

-continued

| Wt. NaI Used | 3.18 g | 3.18 g | 3.18 g | 3.18 g | 2.08 g | 2.77 g | 1.36 g |
|---|---|---|---|---|---|---|---|
| Wt. NaOH Used | 0.85 g | 0.85 g | 0.85 g | 0.85 g | 0.55 g | 0.74 g | 0.36 g |
| Wt. NaOCl Used | 1.58 g | 1.58 g | 1.58 g | 1.58 g | 1.03 g | 1.38 g | 0.68 g |
| Solvent | tert-Butyl Alcohol | Methanol | Ethanol | Methanol | Methanol | Methanol | Methanol |
| Temperature | 0° C. | 0° C. | 0° C. | 40° C. | 0° C. | 0° C. | 0° C. |
| Addition Time | 1.7 h | 1.0 h | 2.5 h | 0.8 h | 0.7 h | 1.2 h | 0.8 h |
| Yield | 81% | 80% | 78% | 67% | 84% | 80% | 78% |
| Product | 4-Iodo-phenol | 4-Iodo-phenol | 4-Iodo-phenol | 4-Iodo-phenol | 6-Iodo-2-naphthol | 4-Iodo-2-cresol | 2,4-Di-iodo-phenol |

| | Example No. 8 | Example No. 9 | Example No. 10 | Example No. 11 | Example No. 12 | Example No. 13 | Example No. 14 |
|---|---|---|---|---|---|---|---|
| Hydroxy-aromatic | 4-Nitro-phenol | 2,6-Di-methyl-phenol | 2-Chloro-phenol | 4-Chloro-phenol | 2-hydroxy-pyridine | 8-hydroxy-quinoline | 2-Phenyl-phenol |
| Wt. NaI Used | 2.16 g | 2.58 g | 2.33 g | 2.33 g | 3.78 g | 2.06 g | 96.86 g |
| Wt. NaOH Used | None | None | 0.62 g | None | 0.84 g | 0.55 g | 24.00 g |
| Wt. NaOCl Used | 1.07 g | 1.22 g | 1.16 g | 1.16 g | 1.56 g | 1.02 g | 42.88 g |
| Solvent | Methanol | Methanol | Methanol | Methanol | Methanol | Methanol | Methanol |
| Temperature | 0° C. | 0° C. | 0° C. | 0° C. | 0° C. | 0° C. | 0° C. |
| Addition Time | 0.8 h | 2.0 h | 1.0 h | 1.0 h | 1.5 h | 1.0 h | 2.0 h |
| Yield | 75% | 87% | 74% | 72% | 48% | 97% | 84% |
| Product | 2-Iodo-4-nitro-phenol | 4-Iodo-2,6-di-methyl-phenol | 4-Iodo-1-chloro-phenol | 2-Iodo-4-chloro-phenol | 2-Hydroxy-5-iodo-pyridine | 8-Hydroxy-5-iodo-quinoline | 4-Iodo-2-phenyl-phenol |

EXAMPLE 15

| | |
|---|---|
| Aminoaromatic | Aniline |
| Wt. NaI Used | 3.22 g |
| Wt. NaOH Used | 0.86 g |
| Wt. NaOCl Used | 1.60 g |
| Solvent | Methanol |
| Temperature | 0° C. |
| Addition Time | 1.0 h |
| Yield | 68% |
| Product | 4-Iodoaniline |

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method for selectively monoiodinating, diiodinating or triiodinating the aromatic ring of a hydroxyaromatic or aminoaromatic compound selected from the group consisting of phenols, naphthols, anilines and hydroxy substituted quinolines and pyridines, comprising the step of:
   (i) dissolving said hydroxyaromatic or aminoaromatic compound and a metal iodine in an alcohol solvent,
   (ii) adding to said alcohol solvent an aqueous solution of a metal hypochlorite at a temperature of −100° C. to 100° C., and
   (iii) neutralizing the resulting solution and isolating the iodinated hydroxyaromatic or aminoaromatic product.

2. The method of claim 1, wherein said metal iodide is selected from the group consisting of alkali and alkaline-earth iodides.

3. The method of claim 2, wherein said alkali iodide is selected from the group consisting of sodium iodide, potassium iodide, and lithium iodide.

4. The method of claim 1, wherein said metal hypochlorite is selected from the group consisting of alkali and alkaline-earth hypochlorites.

5. The method of claim 4, wherein said alkaline hypochlorite is selected from the group consisting of sodium hypochlorite, potassium hypochlorite and lithium hypochlorite.

6. The method of claim 1 wherein said reaction is carried out at a temperature between about −78° C. to 45° C.

7. The method of claim 6, wherein said reaction is carried out at a temperature between about −20° to 20° C.

8. The method of claim 1, wherein said alcohol solvent comprises an alcohol having 1–10 carbon atoms.

9. The method of claim 8, wherein said alcohol is selected from the group consisting of methanol, ethanol, propanol, isopropanol, n-butanol, and tert-butanol.

10. The method of claim 1, wherein a base having a basic equilibrium constant at least equal to that of sodium carbonate is dissolved in said alcohol solvent in said dissolving step.

11. The method of claim 10, wherein said base is sodium carbonate or sodium hydroxide.

* * * * *